US00PP12975P2

(12) United States Plant Patent
den Haan

(10) Patent No.: US PP12,975 P2
(45) Date of Patent: Sep. 17, 2002

(54) MENTHA PLANT NAMED 'SNOWCONES WHITE'

(75) Inventor: Pieter den Haan, Steenbergen (NL)

(73) Assignee: Kieft Seed Holland, Venhuizen (NL)

( * ) Notice: Subject to any disclaimer, the term of this patent is extended or adjusted under 35 U.S.C. 154(b) by 39 days.

(21) Appl. No.: 09/837,566

(22) Filed: Apr. 18, 2001

(51) Int. Cl.[7] ..... A01H 5/00

(52) U.S. Cl. ..... Plt./259

(58) Field of Search ..... Plt./259, 258

*Primary Examiner*—Bruce R. Campell
*Assistant Examiner*—June Hwu
(74) *Attorney, Agent, or Firm*—C. A. Whealy

(57) ABSTRACT

A distinct cultivar of Mentha plant named 'Snowcones White', characterized by its compact, outwardly spreading to cascading plant habit; freely branching growth habit; aromatic dark green foliage; and white-colored flowers arranged in axillary verticillasters.

1 Drawing Sheet

BACKGROUND OF THE INVENTION

The present Invention relates to a new and distinct cultivar of Mentha plant, botanically known as *Mentha pulegium*, and hereinafter referred to by the name 'Snowcones White'.

The new Mentha is a product of a planned breeding program conducted by the Inventor in Steenbergen, The Netherlands. The objective of the breeding program is to create new Menthas with a compact plant habit and attractive flower color. The new Mentha originated from a cross made by the Inventor in 1996 of a proprietary *Mentha pulegium* seedling selection identified as Men-96-O-3, not patented, as the female, or seed parent, with a proprietary *Mentha pulegium* seedling selection identified as Men-96-01-02, not patented, as the male, or pollen parent. The new Mentha was selected as a single plant from the resulting progeny by the Inventor in a controlled environment in Steenbergen, The Netherlands in 1996, on the basis of its compact growth habit and white-colored flowers.

Asexual reproduction of the new cultivar by terminal cuttings taken in a controlled environment in Steenbergen, The Netherlands since 1996, has shown that the unique features of this new Mentha are stable and reproduced true to type in successive generations.

SUMMARY OF THE INVENTION

Plants of the cultivar Snowcones White have not been observed under all possible environmental conditions. The phenotype may vary somewhat with variations in environment and culture such as temperature, light intensity, daylength, water status, and/or fertilizer rate or type without, however, any variance in genotype.

The following traits have been repeatedly observed and are determined to be the unique characteristics of 'Snowcones White'. These characteristics in combination distinguish 'Snowcones White' as a new and distinct cultivar:

1. Compact, outwardly spreading to cascading plant habit.
2. Freely branching growth habit.
3. Aromatic dark green foliage.
4. White-colored flowers arranged in axillary verticillasters.

Plants of the new Mentha differ from plants of the parent selections and known cultivars of Mentha primarily in plant habit as plants of the new Mentha are more compact than plants of the parent selections and other known cultivars of Mentha.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Mentha.

The photograph at the top of the sheet comprises a side perspective view of a typical plant of 'Snowcones White'.

The photograph at the bottom of the sheet comprises a close-up view of typical inflorescences and leaves of 'Snowcones White'.

DETAILED BOTANICAL DESCRIPTION

In the following description, color references are made to The Royal Horticultural Society Colour Chart except where general terms of ordinary dictionary significance are used. Plants grown for 12-weeks in 15-cm containers and pinched once were used for the photographs and following description. Plants were grown in a polycarbonate-covered greenhouse in Lompoc, Calif. during the late winter/early spring with day temperatures ranging form 18 to 24° C., night temperatures ranging from 16 to 18° C., and light levels ranging from 4,000 to 8,000 foot-candles.

Botanical classification: *Mentha pulegium* cultivar Snowcones White.

Parentage:

*Female parent.*—Proprietary *Mentha pulegium* seedling selection identified as Men-96-O-3, not patented.

*Male parent.*—Proprietary *Mentha pulegium* seedling selection identified as Men-96-01-02, not patented.

Propagation:

*Type cutting.*—Terminal cuttings.

*Time to initiate roots, summer and winter.*—About 5 days at 18° C.

*Time to develop roots, summer and winter.*—About 14 days at 18° C.

*Root description.*—Fine, fibrous.

*Rooting habit.*—Freely branching, dense.

Plant description:

*Form.*—Compact and outwardly spreading to cascading growth habit. Lateral branches initially upright, but tend to cascade with subsequent development. Freely branching with about 18 lateral branches developing after pinching. Vigorous.

*Plant height.*—About 25 cm.

*Plant diameter.*—About 50 cm.

*Lateral branches.*—Length: About 48 cm. Diameter: About 3.5 mm. Internode length: Vegetative branches: About 2 cm. Flowering branches: About 4.5 cm. Strength: Flexible, but strong. Texture: Glabrous, smooth. Color: 147D.

*Foliage description.*—Leaves simple, generally symmetrical and long-persisting; opposite; sessile. Length: About 3.5 cm. Width: About 6 mm. Shape: Narrowly elliptic to almost linear. Apex: Acute. Base: Truncate. Margin: Entire. Texture, upper surface: Smooth, glabrous. Texture, lower surface: Smooth, glabrous and grandular. Venation pattern: Pinnate to slightly arcuate. Fragrance: Pennyroyal; aromatic, pungent, menthol-like. Color: Young foliage, upper and lower surfaces: 146A. Mature foliage, upper surface: 147A; venation, 147B. Mature foliage, lower surface: 147A; venation, 147C.

Flower description:

*Flower type and habit.*—Small single flowers arranged in axillary verticillasters, two verticillasters per node; individual flowers face upward or outward depending on position in verticillaster. Freely flowering; about four nodes per lateral branch in flower at one time, with about 70 flowers per verticillaster, or about 560 flowers per flowering branch. Verticillasters and individual flowers, sessile. Flowers self-cleaning.

*Natural flowering season.*—Summer and fall, flowering continuous during this period.

*Flower longevity on the plant.*—About 5 to 7 days.

*Fragrance.*—Pungent, spicy menthol-like.

*Verticillaster height.*—About 1.4 cm.

*Verticillaster diameter.*—About 2.5 cm.

*Flowers.*—Appearance: Actinomorphic, somewhat salverform; four-parted, petals fused at base, separate and somewhat erect towards apex. Diameter: At petal apices: About 4 mm. At petal base, fused: About 1 mm. Height: About 7 mm.

*Flower buds* (*showing color*).—Length: About 4 mm. Diameter: About 1 mm. Shape: Ovoid. Color: 155D.

*Corolla.*—Petal arrangement/appearance: Single whorl of four petals, fused at base and separate towards apices. Petal length: About 6 mm. Petal width: About 1 mm. Petal shape: Ligulate. Petal apex: Rounded. Petal margin: Entire. Petal texture: Smooth, satiny. Petal color: Upper and lower surfaces, when opening: 155D. Upper and lower surfaces, fully opened: 155D, slightly translucent.

*Calyx.*—Quantity/arrangement: One single calyx tube per flower; four fused sepals. Length: About 3 mm. Diameter: About 1.5 mm. Shape: Tubular or cup-shaped. Apex: Acute. Texture: Smooth. Color, both surfaces: 144B to 144C.

*Bracts.*—Quantity/arrangement: Five per axil subtending each verticillaster or 10 per node. Initially enclosing the flower buds, then as inflorescences open, bracts recurved back towards lateral branch. Length: About 5 mm. Width: About 4 mm. Shape: Elliptic. Apex: Acute. Texture: Smooth. Color, both surfaces: 147A.

*Reproductive organs.*—Stamens: Quantity: Four per flower. Anther shape: Ovoid. Anther length: Less than 1 mm. Anther color: 166A. Pollen amount: Scarce. Pollen color: 156C. Pistils: Quantity: One per flower. Pistil length: About 9 mm. Stigma shape: Forked. Stigma color: 155D. Style length: About 7 mm. Style color: 155D. Ovary color: 144B.

*Seed.*—Seed production has not been observed.

Disease/pest resistance: Plants of the new Mentha have not been noted to be resistant to pathogens or pests common to Mentha.

Weather tolerance: Plants of the new Mentha have been observed to be tolerant to rain, wind and temperatures from 4 to 30° C.

It is claimed:

1. A new and distinct cultivar of Mentha plant named 'Snowcones White', as illustrated and described.

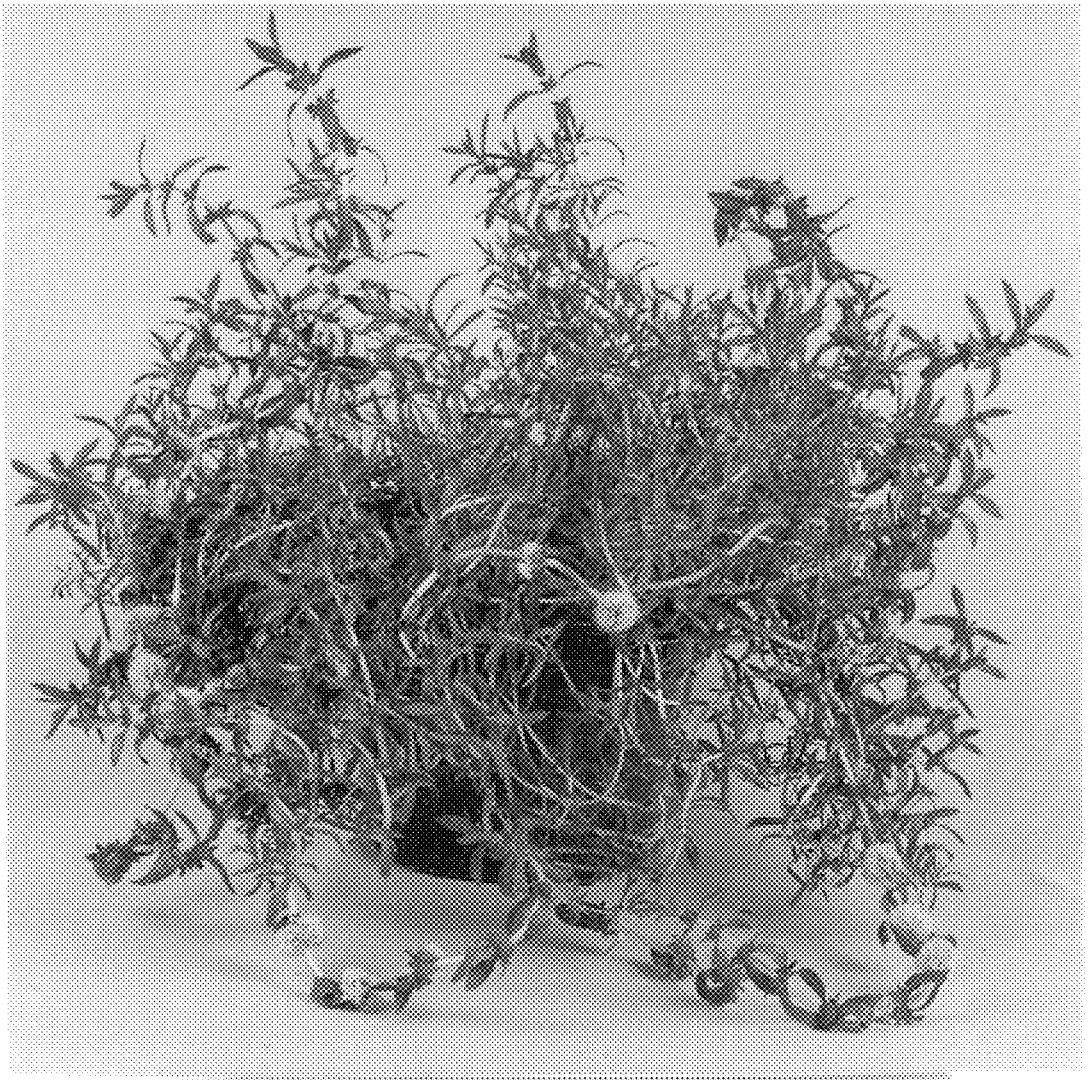
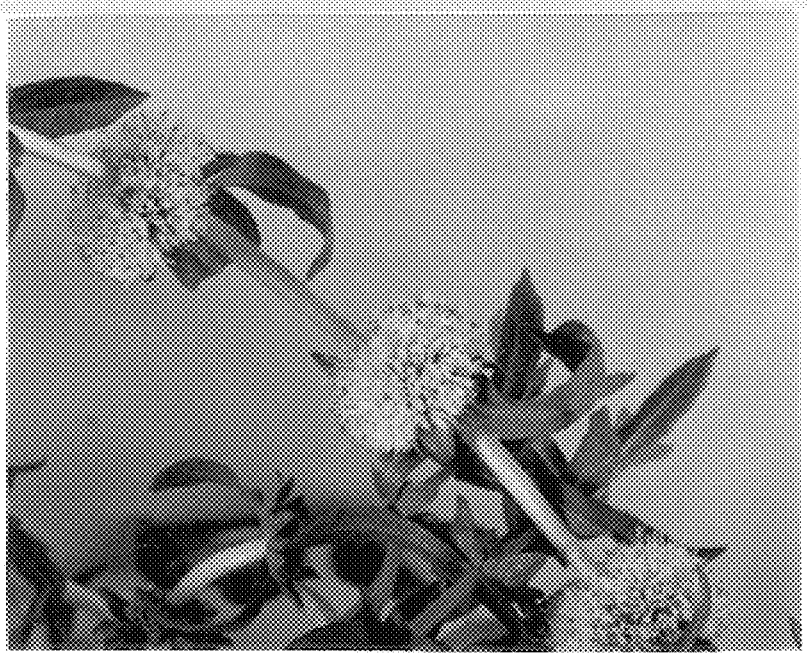

* * * * *